United States Patent [19]

Christoffersen et al.

[11] 4,229,180

[45] Oct. 21, 1980

[54] PROCESS AND CATALYST FOR DETERMINING NITROGEN IN A SAMPLE ACCORDING TO THE KJELDAHL PRINCIPLE

[75] Inventors: Steen R. Christoffersen, Hilleroed; Ole-Christian Bjarno, Holte, both of Denmark

[73] Assignee: A/S N. Foss Electric, Hilleroed, Denmark

[21] Appl. No.: 949,269

[22] Filed: Oct. 6, 1978

[30] Foreign Application Priority Data

Oct. 7, 1977 [DK] Denmark ............................. 4452/77

[51] Int. Cl.$^2$ ..................... G01N 31/10; G01N 31/16; B01J 23/16
[52] U.S. Cl. .................................... 23/230 R; 252/461
[58] Field of Search ....................... 23/230 R; 252/461

[56] References Cited

U.S. PATENT DOCUMENTS

| | | | |
|---|---|---|---|
| 3,335,097 | 8/1967 | Gillis | 252/428 |
| 3,346,659 | 10/1967 | Barclay | 252/461 X |
| 3,525,701 | 8/1970 | Barclay | 252/461 |
| 3,627,817 | 12/1971 | Barnett | 252/461 UX |
| 3,709,829 | 1/1973 | Gasson | 252/461 |
| 3,984,353 | 10/1976 | Sergunkin | 252/461 |

OTHER PUBLICATIONS

Chemical Abstracts, 78: 146344x (1973).

*Primary Examiner*—Sidney Marantz
*Attorney, Agent, or Firm*—Hubbell, Cohen, Stiefel & Gross

[57] ABSTRACT

An antimonate, such as potassium antimonate, is used as the destruction catalyst in nitrogen determinations according to the Kjeldahl principle. Preferred catalyst comprises potassium antimonate together with potassium sulfate (for increasing the boiling point of the destruction mixture) and minor amounts of zinc sulfate and cupric sulfate (as co-catalysts).

17 Claims, No Drawings

PROCESS AND CATALYST FOR DETERMINING NITROGEN IN A SAMPLE ACCORDING TO THE KJELDAHL PRINCIPLE

The present invention relates to a process for determining nitrogen in a sample according to the Kjeldahl principle, and a catalyst for use in the process.

In the Kjeldahl analysis, it is known to use a catalyst for promoting the destruction so that the analysis may be performed in a shorter time. The catalyst must be one which does not give rise to systematic error by forming byproducts consuming part of the nitrogen. A wide range of substances has been tested as catalysts, including for example oxides of titanium, lead, copper, manganese, bismuth, iron and zinc, but the most efficient catalyst and the one used extensively in practice is mercuric oxide, which, inter alia, has the advantage of yielding an especially effective destruction of nicotinic acid. Among nitrogen compounds, nicotinic acid is known to be the most difficult one to destruct, and the incomplete destruction of nicotinic acid will result in a systematic error in the Kjeldahl analysis.

Thus, mercuric oxide has been found to give excellent results as destruction catalyst in the Kjeldahl analysis, both in the conventional Kjeldahl analysis and in the automated Kjeldahl analysis for which a special apparatus has been developed, the so-called "Kjel-Foss Automatic", the construction and principle of which are disclosed in U.S. Pat. No. 3,964,869. However, it is now evident that the environmental and health hazards connected to mercury compounds make it desirable to avoid the use of mercuric oxide in the considerable amounts which are needed when performing a great number of analyses, such as in the automated equipment, and it would be a definite advance to provide a catalyst which is more acceptable than mercuric oxide with respect to environmental and health considerations, but which gives a sufficiently efficient destruction of the nitrogenous compounds, especially nicotinic acid, to ensure that the results of the analyses are sufficiently exact for practical purposes.

It has now been found that this can be obtained by using an antimonate as the catalyst for accelerating the destruction in the determination of nitrogen in a sample according to the Kjeldahl principle. As appears from the data in the examples, the use of an antimonate as the destruction catalyst in amounts which are reasonable and easily adaptable in practice permits the obtainment of such an efficient destruction, especially also of nicotinic acid, that the analysis results obtainable are comparable with the results which could previously only be obtained using mercuric oxide.

U.S. Pat. No. 3,335,097 discloses Kjeldahl destruction catalysts which do not contain mercury. The catalysts in question utilize copper selenite as the active component, but the use of selenium as the catalyst in the Kjeldahl destruction does not show the same advantages as the use of an antimonate, as selenium compounds are generally considered less safe than antimony compounds, and as selenium sublimates at high temperature and is thereby liable to be emitted from the solution due to the high temperature prevailing during the Kjeldahl destruction, cf. the below Example 8.

It is known, for example from British Pat. Nos. 864,666, 904,602, and 1,271,191 and from German Auslegeschrift No. 2,039,497, to use antimony and antimony compounds as catalysts in various chemical processes, but all of these references disclose the use of antimony compounds in syntheses and they do not disclose or indicate the use of antimony or antimony compounds as destruction catalysts.

In the present context, the term "antimonate" is intended to designate a compound of antimony(V), including both true antimonates, that is, salts which are theoretically or in practice derived from antimony(V)acid $HSbO_3$ (or $HSbO_3.3H_2O = H[Sb(OH)_6]$), or hydrates of such salts: $M(SbO_3)y.xH_2O$, especially $M[Sb(OH)_6]y.(x-3)H_2O$, for example leuconin = $NaSbO_3$ or potassium antimonate $K[Sb(OH)_6]$, and the so-called antimonates, that is, mixed oxides of metal oxides and $Sb_2O_5$ and/or $Sb_2O_4$, for example $(PbO)_2.Sb_2O_5 (= Pb_2Sb_2O_7)$, $(PbO)_3.Sb_2O_5 (= Pb_3(SbO_4)_2)$ or hydrates thereof, for example $MgO.Sb_2O_5.12H_2O$.

For the purpose of the present invention it is preferred that the antimonate is potassium antimonate, and in practice, it is preferred to use the commercially available form thereof which is potassium antimonate hemihydrate $K[Sb(OH)_6]\frac{1}{2}H_2O$, and in the following description, the term "potassium antimonate" designates this hemihydrate unless otherwise indicated.

Analogously to the nitrogen determination according to the Kjeldahl principle using other catalysts, the antimonate may be added as a powder, a granulate, or tablets, or it may be added as a solution or slurry in water or, suitably, in a component which is to be added in the destruction anyway, such as hydrogen peroxide or sulfuric acid, or mixtures thereof.

The amount of potassium antimonate used in the Kjeldahl destruction will preferably be between 0.5 and 10 g per g of the sample to be subjected to the Kjeldahl destruction. As will appear from the examples, the completeness of the destruction will increase with increasing amount of antimonate. For use in certain existing equipment, the size of the reaction vessel and suctioning system of the equipment may limit the amount of catalyst which can be used per g of sample, and as an example, in the commercial "Kjel-Foss Automatic", the suitable amount of potassium antimonate per g of sample will be about 1.5–5 g, for example about 2.5 g.

It is often especially suitable to add the antimonate together with salts increasing the boiling point of the destruction mixture, preferably sodium sulfate or potassium sulfate or mixtures thereof, potassium sulfate being preferred. A suitable amount of potassium sulfate per g of the sample to be subjected to the Kjeldahl destruction is about 6–20 g, for example about 10–15 g. An especially suitable application form of the catalyst is tablets which, like the conventional mercuric oxide-containing tablets which are used for example in connection with the automated "Kjel-Foss Automatic", should be prepared without the use of any binders, as binders might give rise to errors in the analyses due to content of nitrogen, either as a structural component or as an impurity. Preferred tablets are tablets having a potassium antimonate content of 0.2–3 g per tablet, and a content of potassium sulfate of 2–5 g per tablet. When the tablets are to be used in existing automatic equipment of the type described above, a potassium antimonate content of 0.5–1.5 g per tablet, for example about 0.8 g per tablet, is suitable when 3 tablets per sample of about 1 g are used in accordance with the usual instructions for the said equipment, as this content of potassium antimonate is suitable in relation to the size of the reaction vessel and the suctioning system of the equipment. In cases where this limitation imposed by the equipment does not apply, but where it is desired to perform the analysis in a corresponding manner with addition of 3 tablets per sample having a sample weight of about 1 g, a potassium antimonate content of 2-3 g per tablet may be used in order to obtain an almost quantitative destruction of nicotinic acid, vide the results in Example 4. The tablets may suitably have a diameter of about 19 mm and a thickness of about 7 mm, and tablets for use in existing "Kjel-Foss Automatic" equipment may be tablets having a content of 0.8 g of potassium antimonate and 4.6 g of potassium sulfate. Tablets are suitably prepared from starting materials of analysis grade and without the use of any binder by moistening a mixture of potassium antimonate powder and finely ground potassium sulfate powder with water and thereafter compressing the moistened mixture into tablets.

When the potassium antimonate is used in a solution or slurry, it is especially suitable to use potassium antimonate mixed with concentrated sulfuric acid in an amount of 0.2-2.0 g/ml, especially an amount of 0.6-0.8 g/ml.

When a different antimonate is used instead of potassium antimonate, the weight amounts of the antimonate are adjusted correspondingly.

As mentioned above, the antimonate catalyst is of special importance in connection with the automated nitrogen determination according to the Kjeldahl principle, for example using "Kjel-Foss Automatic", and this especially important embodiment of the process of the invention comprises performing, in the automated Kjeldahl analysis, the following destruction stages which each takes about 3 minutes:

(a) a sample of about 1 g is placed in a flask, catalyst and salt for increasing the boiling point of the destruction mixture are added in tablet form, and hydrogen peroxide and concentrated sulfuric acid are added, (b) the destruction mixture is heated to boiling at about 400° C., during which water and hydrogen peroxide are evaporated or consumed, (c) the destruction mixture is kept at the boiling point, with a temperature rise to at the most 410° C.

As mentioned above, it is preferred to use, in stage (a), 3 tablets having the preferred content of potassium antimonate and potassium sulfate as explained above, about 9 ml of 35% hydrogen peroxide, and 10-16 ml of concentrated sulfuric acid.

As will be seen from the results reported in the below examples, the nitrogen contents found using the catalyst of the present invention are very close to the nitrogen contents found using mercuric oxide as the destruction catalyst, the deviation between the mercuric oxide catalyst and the catalyst of the present invention being almost negligible when antimonate amounts in the higher part of the above-mentioned ranges are used. However, even though the use of antimonate amounts in the lower part of the range may give rise to a certain small deviation, this can easily be overcome, with retainment of the advantages provided by the present invention, by performing the small correction necessary to bring the nitrogen contents found with the antimonate catalyst in conformity with the contents found with mercuric oxide. The necessary correction parameters can be found empirically in connection with the particular analysis routine, and examples of such corrections with either a correction factor or a correction factor + a constant are given in Examples 5 and 6.

Another way to obtain maximum conformity with nitrogen contents found by Kjeldahl destruction using mercuric oxide as the destruction catalyst is to combine the antimonate catalyst with minor amounts of co-catalysts. Co-catalysts which have been found effective for obtaining conformity between the nitrogen values found using on the one hand mercuric oxide and on the other hand antimonate amounts in the lower part of the above-mentioned range, are copper, zinc, and cobalt compounds, among which copper and zinc compounds are preferred as they are considered more safe, from an environmental and health point of view, than cobalt compounds. Although copper compounds may also not be desirable in greater amounts, it has been found that a suitable co-catalyst combination is a combination comprising a minimum amount of copper compound combined with a somewhat larger amount of zinc compound. Suitable amounts of cobalt and zinc compounds for use as co-catalysts are for example about 0.15-1.2 g, preferably about 0.3-0.9 g, and especially about 0.6 g, of zinc sulfate heptahydrate and about 0.03-1 g, preferably about 0.1-0.3 g, and especially about 0.2 g, of cupric sulfate pentahydrate, per g of the sample to be subjected to the destruction. If other zinc or copper compounds are used, their relative amount may be adjusted accordingly, and in principle, any zinc and copper salt having a suitable nitrogen-free anion may be employed.

When the antimonate catalyst of the invention is formulated as tablets in accordance with the principles discussed above, corresponding suitable amounts of co-catalysts are about 0.05-0.4, suitably about 0.1-0.3, for example 0.2, g of zinc sulfate heptahydrate per tablet and 0.01-0.3, suitably about 0.03-0.1, for example about 0.07, g of cupric sulfate pentahydrate per tablet. A specific example of a preferred tablet containing a co-catalyst is a tablet with a content of 0.8 g of potassium antimonate, 4.8 g of potassium sulfate, 0.2 g of zinc sulfate heptahydrate, and 0.07 g of cupric sulfate pentahydrate.

The catalyst of the present invention is used in the destruction stage of analyses according to the Kjeldahl principle, either performed according to the conventional Kjeldahl method or according to the above-described automated Kjeldahl process. The other stages in the Kjeldahl analysis, whether conventional or automated, are performed in the usual way.

According to one special aspect of the present invention, the antimonate and optionally the above-mentioned preferred co-catalysts may be used in combination with one or more other Kjeldahl destruction catalysts, for example $TiO_2HgO$ or $ZrO_2$. However, a satisfactory destruction of even nicotinic acid may be obtained already using the antimonate alone or in combination with zinc or copper as co-catalysts, and from the above-mentioned environmental and health considerations, it will usually be preferred to use a catalyst of the invention without any addition of mercuric oxide.

The invention is illustrated through the following examples which are not to be construed as limiting.

EXAMPLES 1-3

In Examples 1-3 the nitrogen contents of 0.5 g samples of pork, rape, soy bean meal and nicotinic acid were determined according to the Kjeldahl principle in a "Kjel-Foss Automatic" using as catalyst 0.75 g of mercuric oxide, 1 g of potassium antimonate, and 1 g of titanium dioxide, respectively. The run with mercuric oxide was used as a reference. The determinations were performed according to the usual method.

The results found are stated in the below Table I, wherein the amount of nitrogen found is stated as compared to the amount found with mercuric oxide (refound amount) together with the standard deviation on the percentage found in the test in question. The reproducibility was calculated on the basis of 5 measurements.

TABLE I.

| Example | | 1 | 2 | 3 |
|---|---|---|---|---|
| Run | Catalyst<br>Test Material | HgO | K[Sb(OH)$_6$]<br>(Reference) | TiO$_2$ |
| a | Pork | 100%<br>1.6% | 99.1%<br>0.96% | 62.8%<br>11% |
| b | Rape | 100%<br>0.4% | 99.6%<br>0.4% | 99.1%<br>0.5% |
| c | Soy bean meal | 100%<br>0.24% | 100.6%<br>0.7% | 97.2%<br>1.2% |
| d | Nicotinic acid | 100%<br>0.7% | 49.8%<br>3.3% | 39.0%<br>7.8% |
| | Mean value of the refound amount in runs a-c | 100%<br>0.75% | 99.8%<br>0.7% | 86.4%<br>4.2% |

EXAMPLE 4

In a "Kjel-Foss Automatic" destructions of nicotinic acid were made using various amounts of potassium antimonate powder. The results are stated in the below Table II as the refound content of nitrogen in percent of the amount found with 0.75 g of mercuric oxide.

Table II.

| Amount of potassium antimonate used, g | 1 | 2 | 3 | 4 | 5 | 6 |
|---|---|---|---|---|---|---|
| Refound content of nitrogen, % | 34.5 | 48.6 | 62.8 | 77.0 | 89.3 | 98.2 |

Apart from the amount of catalyst added, the determination of nitrogen was carried out in the usual manner.

As appears from the above results, an almost 100% destruction was obtained using an amount of potassium antimonate of 6 g per g of test material.

EXAMPLES 5-6

In a "Kjel-Foss Automatic", the nitrogen content was determinated in a wide range of nitrogen-containing substrates according to the usual procedure. In Example 5, 3 of the commercial "Foss-Tabs", each containing 0.25 g of mercuric oxide and 5 g of potassium sulfate, were used, whereas in Example 6, 3 tablets, each containing 0.8 g of potassium antimonate and 4.6 g of potassium sulfate were used. The nitrogen contents determined with mercuric oxide and the amounts of nitrogen refound with potassium antimonate are stated in the below Table III together with their respective standard deviations. In cases where the refound value was below 97% or above 99% as well as in cases where the reproducibility was especially bad, 10 or 20 determinations were performed. In column %N$_{Sb}$ corr. are stated the values obtained after the necessary small correction of the values found with the potassium antimonate catalyst, and in the column "dr(%)" are stated the deviations between the thus corrected values and the values found with the mercuric oxide catalyst. In the correction, the formula %N corr.=%N found×1.0252 was used for nitrogen contents below 3.5%, whereas the formula %N corr.=%N found×1.0074+0.070 was used for nitrogen contents above 3.5%. These algorithms were determined empirically.

TABLE III.

| Product | Number of samples | Example 5<br>Mercuric oxide | | Example 6<br>Potassium antimonate | | % refound | %N$_{Sb}$ corr. | dr(%) |
|---|---|---|---|---|---|---|---|---|
| | | %N | Sr(%) | %N | Sr(%) | | | |
| Soup | 4 | 2.00 | 0.64 | 1.95 | 1.2 | 97.5 | 2.00 | 0 |
| Almonds | 4 | 4.02 | 0.60 | 3.95 | 0.4 | 98.2 | 4.04 | 0.50 |
| Egg powder | 4 | 1.92 | 0.21 | 1.85 | 0.4 | 96.6 | 1.90 | 0.99 |
| Maize | 4 | 1.43 | 0.18 | 1.41 | 0.66 | 98.6 | 1.45 | 1.39 |
| Soy meal | 4 | 3.57 | 0.47 | 3.48 | 0.55 | 97.3 | 3.58 | 0.16 |
| Coconut expellets | 4 | 3.30 | 0.77 | 3.22 | 0.77 | 97.6 | 3.30 | 0 |
| Palm oil cake | 4 | 2.64 | 0.61 | 2.59 | 0.36 | 98.1 | 2.66 | 0.75 |
| Gelatine | 4 | 4.77 | 0 | 4.62 | 0 | 96.9 | 4.72 | 0.96 |
| Linseed | 4 | 3.54 | 1.85 | 3.44 | 1.35 | 97.2 | 3.53 | 0.38 |
| Wheat bran | 4 | 2.22 | 0.72 | 2.18 | 1.78 | 98.2 | 2.23 | 0.45 |
| Milk powder | 4 | 5.71 | 0.28 | 5.62 | 0.14 | 98.4 | 5.74 | 0.52 |
| Sesame cake | 4 | 7.52 | 0.17 | 7.42 | 0.12 | 98.7 | 7.54 | 0.33 |
| Green fodder meal | 4 | 2.86 | 1.6 | 2.80 | 1.2 | 97.9 | 2.87 | 0.35 |
| Mash | 4 | 5.26 | 0.58 | 5.17 | 0.93 | 98.3 | 5.28 | 0.35 |
| Milupa | 4 | 2.10 | 0.99 | 2.05 | 0.39 | 97.6 | 2.10 | 0 |
| Broad beans | 4 | 4.42 | 0.47 | 4.35 | 0.55 | 98.4 | 4.45 | 0.68 |
| Casein | 4 | 7.25 | 0.13 | 7.1 | 0.67 | 98.2 | 7.22 | 0.41 |
| Spice mixture | 4 | 1.43 | 1.2 | 1.39 | 0.99 | 97.2 | 1.43 | 0 |
| Liver paste | 4 | 2.11 | 0.6 | 2.06 | 1.7 | 97.6 | 2.11 | 0 |
| Barley | 4 | 1.68 | 0.95 | 1.65 | 1.1 | 98.2 | 1.69 | 0.59 |
| Rat faeces | 4 | 0.665 | 0 | 0.645 | 1.1 | 97.0 | 0.661 | 0.56 |
| L-Proline | 4 | 6.1 | 0.29 | 6.0 | 0.35 | 98.5 | 6.11 | 0.23 |
| L-Histidine | 4 | 6.75 | 0.30 | 6.62 | 0.83 | 98.1 | 6.74 | 0.16 |
| Fish meal | 10 | 5.35 | 1.13 | 5.2 | 0.80 | 97.2 | 5.31 | 0.78 |
| Acetanilide | 10 | 5.20 | 0.40 | 5.10 | 0.51 | 98.1 | 5.21 | 0.15 |
| Blood meal | 10 | 7.35 | 0.30 | 7.25 | 0.27 | 98.6 | 7.37 | 0.32 |
| Cotton seed expellets | 10 | 1.57 | 0.46 | 1.53 | 0.56 | 97.1 | 1.57 | 0 |
| DL-Tryptophan | 10 | 6.70 | 0.81 | 6.55 | 0.60 | 98.1 | 6.67 | 0.47 |
| Cheese 30% | 10 | 7.70 | 0.33 | 7.50 | 0.46 | 97.4 | 7.66 | 0.52 |
| "Nesquick" | 10 | 0.84 | 0.76 | 0.82 | 0.63 | 97.6 | 0.84 | 0 |
| L-Lysin, HCl | 10 | 7.65 | 0.42 | 7.60 | 0.32 | 99.2 | 7.73 | 1.00 |
| Pork | 20 | 3.17 | 2.17 | 3.05 | 1.21 | 96.2 | 3.13 | 1.26 |

TABLE III.-continued

| Product | Number of samples | Example 5 Mercuric oxide %N | Example 5 Mercuric oxide Sr(%) | Example 6 Potassium antimonate %N | Example 6 Potassium antimonate Sr(%) | % re-found | %N$_{Sb}$ corr. | dr(%) |
|---|---|---|---|---|---|---|---|---|
| Frankfurters | 20 | 2.35 | 1.83 | 2.29 | 0.84 | 97.4 | 2.35 | 0 |
| Meat-and-bone meal | 20 | 3.96 | 1.56 | 3.83 | 1.11 | 96.7 | 3.93 | 0.80 |
| Nicotinic acid amide | 10 | 5.70 | 0.65 | 5.58 | 0.47 | 97.9 | 5.69 | 0.15 |
| Danish salami | 20 | 2.30 | 2.16 | 2.25 | 0.95 | 97.8 | 2.31 | 0.43 |

EXAMPLE 7

Tablets containing 0.8 g of potassium antimonate, 0.2 g of zinc sulfate heptahydrate, 0.07 g of cupric sulfate pentahydrate and 4.8 g of potassium sulfate, were compared with "Foss-Tabs" having the composition stated in Example 5.

The protein content was determined in various materials for the fodder production (Table IV) and in various meat products (Table V), and the nitrogen content was determined in various pure compounds (Table VI).

The "setting for H$_2$SO$_4$" indicates the number of ml of concentrated sulfuric acid added in accordance with the following scheme:

| Setting for H$_2$SO$_4$ | ml of concentrated sulfuric acid |
|---|---|
| 40 | 12.4 |
| 25 | 11.7 |
| 45 | 12.6 |
| 48 | 12.7 |
| 50 | 12.8 |
| 70 | 13.4 |

It was found unnecessary to correct the protein contents determined with the catalyst tablets of the invention.

TABLE IV.

| Test material | Sample weight, g | Setting for H$_2$SO$_4$ | Catalyst | Number of samples | Protein contents found, % | Relative standard deviation, % | Refound contents of protein, % |
|---|---|---|---|---|---|---|---|
| Cotton seed expellets | 0.5 | 40 | Hg | 20 | 19.93 | 1.74 | |
|  | 0.5 | 40 | Sb | 19 | 20.15 | 2.65 | 100.1 |
| Milk Powder | 0.5 | 40 | Hg | 6 | 26.78 | 0.37 | |
|  | 0.5 | 40 | Sb | 6 | 26.93 | 0.45 | 100.6 |
| Rape | 1.0 | 70 | Hg | 12 | 21.14 | 0.4 | |
|  | 0.5 | 50 | Sb | 20 | 21.26 | 0.9 | 100.6 |
| Fish meal | 0.5 | 40 | Hg | 20 | 67.4 | 0.7 | |
|  | 0.5 | 40 | Sb | 20 | 67.5 | 0.7 | 100.1 |
| Coconut expellets | 1.0 | 48 | Hg | 20 | 20.8 | 1.0 | |
|  | 1.0 | 48 | Sb | 20 | 20.9 | 0.6 | 100.5 |
| Green fodder meal | 0.5 | 40 | Hg | 19 | 17.45 | 3.1 | |
|  | 0.5 | 40 | Sb | 19 | 17.61 | 3.0 | 100.9 |
| Palm cake | 1.0 | 45 | Hg | 20 | 16.89 | 1.2 | |
|  | 1.0 | 45 | Sb | 20 | 16.82 | 1.7 | 99.7 |
| Meat-and-bone meal | 0.5 | 40 | Hg | 20 | 49.4 | 0.4 | |
|  | 0.5 | 40 | Sb | 20 | 49.8 | 0.6 | 100.8 |
| Barley | 1.0 | 40 | Hg | 19 | 9.0 | 1.8 | |
|  | 1.0 | 40 | Sb | 19 | 9.1 | 2.5 | 101.1 |
| Blood meal | 0.5 | 40 | Hg | 16 | 91.39 | 0.41 | |
|  | 0.5 | 40 | Sb | 20 | 92.06 | 0.38 | 100.7 |
| Mean value |  |  |  |  |  | 1.1 | |
|  |  |  |  |  |  | 1.3 | 100.6 |

TABLE V.

| Test material | Sample weight, g | Setting for H$_2$SO$_4$ | Catalyst | Number of samples | Protein contents found, % | Relative standard deviation, % | Refound contents of protein, % |
|---|---|---|---|---|---|---|---|
| Bacon | 0.5 | 40 | Hg | 20 | 16.58 | 1.7 | |
|  | 0.5 | 40 | Sb | 20 | 17.03 | 1.4 | 102.7 |
| Ham sausage | 0.5 | 40 | Hg | 20 | 15.56 | 2.1 | |
|  | 0.5 | 40 | Sb | 20 | 15.80 | 2.8 | 101.5 |
| Liver paste | 0.5 | 40 | Hg | 20 | 9.4 | 4.2 | |
|  | 0.5 | 40 | Sb | 20 | 9.3 | 4.3 | 98.9 |
| Danish salami | 0.5 | 40 | Hg | 20 | 14.8 | 2.0 | |
|  | 0.5 | 40 | Sb | 18 | 14.8 | 2.0 | 100.0 |
| Pork | 0.5 | 40 | Hg | 20 | 21.6 | 1.4 | |
|  | 0.5 | 40 | Sb | 20 | 21.9 | 0.9 | 101.4 |
| Beef | 0.5 | 40 | Hg | 20 | 20.67 | 1.3 | |
|  | 0.5 | 40 | Sb | 20 | 21.02 | 1.7 | 101.7 |
| Mean value |  |  |  |  |  | 2.1 | |
|  |  |  |  |  |  | 2.2 | 101.0 |

TABLE VI.

| Test material | Sample weight, g | Setting for H$_2$SO$_4$ | Catalyst | Number of samples | Protein contents found, % | Relative standard deviation, % | Refound contents of protein, % |
|---|---|---|---|---|---|---|---|
| Nicotinic acid | 0.5 | 25 | Hg | 20 | 11.36 | 0.3 | |
| | 0.5 | 25 | Sb | 19 | 10.80 | 1.2 | 95.1 |
| Acetanilide | 0.5 | 25 | Hg | 19 | 10.36 | 0.9 | |
| | 0.5 | 40 | Sb | 19 | 10.40 | 1.1 | 100.4 |
| Casein | 0.5 | 40 | Hg | 20 | 14.98 | 0.5 | |
| | 0.5 | 40 | Sb | 20 | 14.96 | 0.5 | 99.9 |
| L-Proline | 0.5 | 40 | Hg | 10 | 12.21 | 0.3 | |
| | 0.5 | 40 | Sb | 10 | 12.11 | 0.6 | 98.6 |
| L-Lysine | 0.5 | 40 | Hg | 20 | 15.34 | 0.3 | |
| | 0.5 | 40 | Sb | 20 | 15.14 | 0.5 | 98.7 |
| DL-Tryptophan | 0.5 | 40 | Hg | 20 | 13.59 | 0.16 | |
| | 0.5 | 40 | Sb | 18 | 13.53 | 0.34 | 99.6 |
| KNO$_3$ | 0.5 | 40 | Hg | 20 | 0.085 | | |
| | 0.5 | 40 | Sb | 20 | 0.395 | | |
| Mean value (without nicotinic acid) | | | | | | 0.5 | |
| | | | | | | 0.8 | 99.4 |

EXAMPLE 8

The protein content of fish meal was determined in a "Kjel-Foss Automatic". "Foss-Tabs" (0.25 g of mercuric oxide, 5 g of potassium sulfate) were used as reference, and their efficiency was compared with the efficiency of tablets containing 0.8 g of potassium antimonate and 4.6 g of potassium sulfate ("Sb tabs"), tablets containing 0.8 g of potassium antimonate, 0.2 g of zinc sulfate heptahydrate, 0.07 g of cupric sulfate pentahydrate and 4.8 g of potassium sulfate ("Sb/Zn/Cu tabs"), and powdery mixtures containing zirconium dioxide, titanium dioxide, and selenium dioxide, respectively, both as the sole catalyst and in admixture with cupric sulfate pentahydrate as co-catalyst. Each determination was performed 10 times. The results appear from the below Table VII:

TABLE VII.

Protein determination in fish meal.

| Catalyst | Protein content, % | Relative standard deviation, % | Refound content of protein,% |
|---|---|---|---|
| 3 Foss-Tabs | 67.4 | 0.7 | x |
| 3 Sb/Zn/Cu tabs | 67.5 | 0.7 | 100.1 |
| 3 Sb tabs | 66.7 | 0.5 | 97.4 |
| 0.75 g zirconium dioxide 15 g potassium sulfate | 65.4 | 1.3 | 97.0 |
| 0.2 g zirconium dioxide 0.95 g copper sulfate pentahydrate 15 g potassium sulfate | 65.5 | 0.7 | 97.2 |
| 0.9 g titanium dioxide 15 g potassium sulfate | 63.8 | 8.1 | 94.7 |
| 0.45 g titanium dioxide 0.7 g copper sulfate pentahydrate 15 g potassium sulfate | 65.4 | 2.6 | 97.0 |
| 1.0 g selenium dioxide 15 g potassium sulfate | 66.1 | 0.8 | 98* |
| 0.5 g selenium dioxide 0.65 g copper sulfate pentahydrate 15 g potassium sulfate | 66.6 | 0.8 | 98.8* |

*free selenium sublimated and was deposited as a layer at the neck and the cover of the flask.

EXAMPLE 9

In a similar manner as in Example 8, the efficiency of antimonate in combination with cupric sulfate pentahydrate, zinc sulfate heptahydrate, nickel sulfate hexahydrate and cobalt sulfate heptahydrate, respectively, was compared with the efficiency of "Foss-Tabs" in the destruction of fish meal.

In the below Table VIII, the amount of protein refound with the potassium antimonate catalyst is stated in comparison with the amount found with "Foss Tabs", together with the standard deviations of the protein content determined. It will be noted that nickel does not show any significant co-catalyst effect.

TABLE VIII.

| Catalyst | Number of determinations | Relative standard deviation, % | Efficiency of destruction, amount refound, % |
|---|---|---|---|
| Foss-Tabs | 17 | 0.68 | |
| 0.3 g CuSO$_4$ . 5H$_2$O 2.4 g KSb(OH)$_6$ 15 g K$_2$SO$_4$ | 17 | 0.88 | 99.1 |
| Foss-Tabs | 18 | 0.99 | |
| 0.3 g ZnSO$_4$ . 7H$_2$O 2.4 g KSb(OH)$_6$ 15 g K$_2$SO$_4$ | 14 | 0.50 | 99.0 |
| Foss-Tabs | 17 | 0.79 | |
| 0.3 g NiSO$_4$ . 6H$_2$O 2.4 g KSb(OH)$_6$ 15 g K$_2$SO$_4$ | 17 | 0.77 | 98.0 |
| Foss-Tabs | 14 | 0.78 | |
| 0.3 g CoSO$_4$ . 7H$_2$O 2.4 g KSb(OH)$_6$ 15 g K$_2$SO$_4$ | 14 | 0.50 | 99.5 |

What we claim is:

1. A process for determining nitrogen in a sample according to the Kjeldahl principle, comprising catalyzing the sample destruction with an antimonate.

2. A process according to claim 1 in which the antimonate is potassium antimonate.

3. The process according to claim 1, further comprising adding a salt which increases the boiling point of the Kjeldahl type destruction mixture.

4. The process according to claim 3, wherein the salt for increasing the boiling point is selected from the group consisting of sodium sulfate and potassium sulfate.

5. The process of claim 4, further comprising adding a co-catalyst selected from the group consisting of a zinc salt, a copper salt and mixtures of a zinc and copper salt.

6. The process of claim 5, wherein the co-catalyst is a zinc salt.

7. The process of claim 5, wherein the co-catalyst is a copper salt.

8. The process of claim 5, wherein the co-catalyst is a mixture of zinc and copper salts.

9. A catalyst for use in Kjeldahl type destructions comprising tablets of a potassium antimonate together with a salt selected from the group consisting of sodium sulfate and potassium sulfate.

10. A catalyst according to claim 9, in the form of tablets, each tablet comprising 0.2–3 g of potassium antimonate, and 2–5 g of potassium sulfate.

11. A catalyst according to claim 10 in which each tablet contains 0.5–1.5 g of potassium antimonate.

12. A catalyst according to claim 11 in which each tablet contains about 0.8 g of potassium antimonate, about 0.2 g of zinc sulfate heptahydrate, about 0.07 g of cupric sulfate pentahydrate and about 4.8 g of potassium sulfate.

13. A catalyst according to claims 9, 10 or 11, further comprising a co-catalyst selected from the group consisting of a zinc salt, a copper salt, and mixtures of zinc and copper salts.

14. The catalyst according to claim 13, wherein the co-catalyst is a copper salt.

15. The catalyst according to claim 13, wherein the co-catalyst is a zinc salt.

16. The catalyst according to claim 13, wherein the co-catalyst is both a zinc and a copper salt.

17. A catalyst for use in a Kjeldahl type destruction mixture consisting of tablets of an antimonate and a salt which increases the boiling point of a Kjeldahl type destruction mixture.

* * * * *